United States Patent [19]

Resnick

[11] 4,345,092

[45] Aug. 17, 1982

[54] PROCESS FOR ALKYL PERFLUORO(4,7-DIOXA-5-METHYL-8-FLUOROFORMYLNONANOATE

[75] Inventor: Paul R. Resnick, Wilmington, Del.

[73] Assignee: E. I. Du Pont de Nemours and Company, Wilmington, Del.

[21] Appl. No.: 175,273

[22] Filed: Aug. 4, 1980

[51] Int. Cl.$^3$ ............................................. C07C 67/343
[52] U.S. Cl. ..................................................... 560/182
[58] Field of Search ........................... 560/180, 184, 182

[56] References Cited

U.S. PATENT DOCUMENTS

| | | | |
|---|---|---|---|
| 3,674,820 | 7/1972 | Pittman et al. | 560/184 |
| 4,131,740 | 12/1978 | England | 560/180 |
| 4,138,426 | 2/1979 | England | 560/180 |
| 4,153,804 | 5/1979 | Yamabe et al. | 560/183 |

*Primary Examiner*—Natalie Trousof

*Assistant Examiner*—L. Hendriksen

[57] ABSTRACT

Improved process for making an alkyl perfluoro(4,7-dioxa-5-methyl-8-fluoroformylnonanoate) from hexafluorpropylene oxide and either a monoalkyl difluoromalonyl fluoride or an alkyl perfloro(4-oxa-5-fluoroformylhexanoate) in the presence of fluoride ion catalyst which comprises carrying out the reaction in the presence of a medium consisting essentially of two aprotic liquids, one of the liquids in major proportion and being a poor solvent for methyl perfluoro(4-oxa-5-fluoroformylhexanoate), and the other liquid in minor proportion, being a good solvent for the same compound and being a solvent for the fluoride ion catalyst to the extent of at least 0.001% by weight at 20° C. The product is an intermediate to a valuable fluorinated comonomer used for making fluorinated ion exchange resins.

10 Claims, No Drawings

PROCESS FOR ALKYL PERFLUORO(4,7-DIOXA-5-METHYL-8-FLUOROFORMYLNONANOATE)

BACKGROUND OF THE INVENTION

1. Field of the Invention

This invention relates to improvements in the process for preparing alkyl perfluoro (4,7-dioxa-5-methyl-8-fluoroformylnonanoate)s.

2. Prior Art

Alkyl perfluoro(4,7-dioxa-5-methyl-8-fluoroformylnonanoate)s,

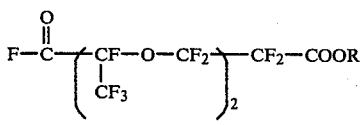   I where R is alkyl of 1–6 carbon atoms, are known compounds. They are used to make, e.g., by pyrolysis, the vinyl esters

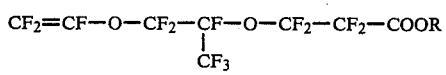   II which have been copolymerized with other fluorinated olefins such as tetrafluoroethylene to provide copolymers which can be fabricated into membranes useful for separating the anode and cathode compartments of a chloralkali cell.

A process for preparing compounds of the formula

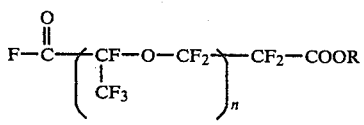   III where R is alkyl of 1–6 carbon atoms and n is 1–6 is disclosed and claimed in U.S. Pat. No. 4,131,740. In that process, a compound of the formula

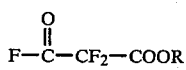   IV is contacted with hexafluoropropylene oxide (HFPO), preferably in the presence of fluoride ion as catalyst. It is disclosed that the fluoride catalyst is usually used in conjunction with an inert liquid diluent (preferably an organic liquid) in which the selected fluoride is at least 0.001% soluble, and that suitable diluents include ethylene glycol dimethyl ether, diethylene glycol dimethyl ether, tetraethylene glycol dimethyl ether, and aprotic solvents such as acetonitrile. In Examples 2 and 3 thereof,

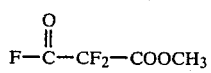   V was reacted with hexafluoropropylene oxide (HFPO) in the presence of fluoride catalyst and tetraglyme as diluent, to make

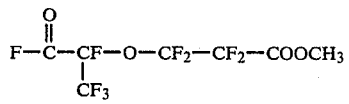   VI which can be further reacted with HFPO as shown in Example 6. In Examples 4 and 5 thereof, V was reacted with HFPO in the presence of cesium fluoride catalyst and tetraglyme as diluent to make a mixture of products III (R=CH₃), n=1–6, including both VI and

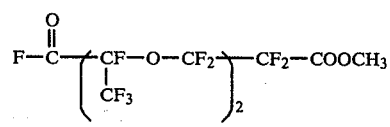   VII

Yields (i.e., yields corrected when possible by allowing for the amount of starting material recovered) to useable compounds VI and VII for these reactions, and E/O ratios (refer to the paragraph preceding the Examples below for the definition of E/O ratio) are given in Table I.

TABLE I

| Example | Yield (%) Based on HFPO | | Yield (%) Based on V | | E/O Ratio |
|---|---|---|---|---|---|
| | to VI | to VII | to VI | to VII | |
| 3 | 12.9 | | 21.1 | | |
| 4 | 4.3 | 7.2 | 9.1 | 7.5 | 2.53 |
| 5 | 23.7 | 14.3 | 51.5 | 15.6 | 0.71 |

In Example 6 thereof, VI was reacted with HFPO in the presence of cesium fluoride and tetraglyme to make VII and compound III (R=CH₃), n=3; the yield of VII based on VI was 11% and based on HFPO was 20.5%, and the E/O ratio was 0.36.

It is clear that the process described in U.S. Pat. No. 4,131,740 gives a mixture of products III wherein different numbers of moles of hexafluoropropylene oxide have been added to the reactant IV. However, when a specific product is desired, e.g., III where n is 2 (i.e., compound I), loss of reactants to concurrent production of substantial amounts of other products, e.g., III where n is 1 and 3–6, is undesirable. Because the reactants IV and HFPO are costly to make, reactant IV being particularly so, loss of starting materials to other products when only compound I is desired incurs substantial loss of valuable precursor compounds.

Accordingly, it is an object of this invention to provide an improved process for making compound I in substantially higher yield than heretofore possible.

SUMMARY OF THE INVENTION

According to the present invention, there is provided an improved process for making compound I in a medium which is a mixture of two components which meet specific criteria.

More specifically, there is provided according to the invention an improved process for preparing a compound of the formula

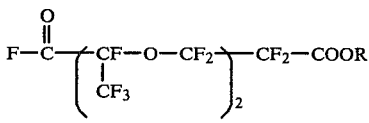

where R is alkyl of 1-6 carbon atoms, wherein a reactant of the formula

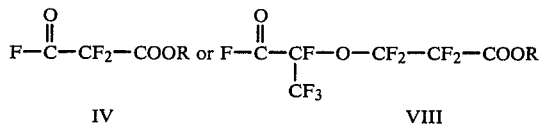

where R is as defined above is contacted with hexafluoropropylene oxide in the presence of fluoride ion as catalyst, the improvement comprising contacting said reactant with hexafluoropropylene oxide and said catalyst in the presence of a medium consisting essentially of two components, component A being 50 to 98% by volume of an aprotic liquid in which methyl perfluoro(4-oxa-5-fluoroformylhexanoate) dissolves to the extent of less than 10 g/100 g of A at 20° C., and component B being 50 to 2% by volume of an aprotic liquid in which said catalyst is soluble to the extent of at least 0.001% by weight at 20° C. and in which methyl perfluoro(4-oxa-5-fluoroformylhexanoate) dissolves to the extent of at least 10 g/100 g of B at 20° C.

DETAILED DESCRIPTION OF THE INVENTION

In the process of the invention, a monoalkyl difluoromalonyl fluoride,

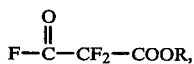   IV or an alkyl perfluoro(4-oxa-5-fluoroformylhexanoate),

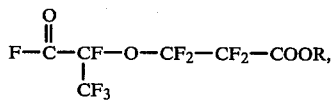   VIII where the alkyl (R) has 1 to 6 carbon atoms, is reacted with hexafluoropropylene oxide in the presence of fluoride ion catalyst and in contact with a medium consisting essentially of two components, A and B.

The first component (A) is an aprotic liquid in which methyl perfluoro(4-oxa-5-fluoroformylhexanoate) dissolves to the extent of less than 10 g/100 g of A, preferably to the extent of no more than 6 g/100 g of A, at 20° C. Suitable examples of component A include dinitriles such as malono-, succino-, glutaro-, adipo-, methylmalono-, pimelo-, subero-, and phthalo-nitrile; and tetramethylenesulfone. The dinitriles are preferred, and adiponitrile is especially preferred.

The second component (B) is an aprotic liquid in which the fluoride catalyst is soluble to the extent of at least 0.001% by wt. at 20° C., and in which methyl perfluoro(4-oxa-5-fluoroformylhexanoate) dissolves to the extent of at least 10 g/100 g of B, preferably to the extent of at least 20 g/100 g of B, and especially preferably to the extent of at least 100 g/100 g of B, at 20° C. Suitable examples of component B include the so-called glymes (mono-, di-, tri- and tetraethyleneglycol dimethyl ether); lactones such as 4-butyrolactone, 5-valerolactone and 6-caprolactone, and mononitriles such as acetonitrile and propionitrile. Triglyme and tetraglyme are preferred because they are more easily separated from compound VII.

Component A is used in the medium in an amount of about 50 to 98% by volume and, correspondingly, component B is in an amount of 50 to 2% by volume. Preferably, component A constitutes 85 to 98% by volume of the medium, and component B is 15 to 2% by volume. In the most preferred aspect of the invention, component A constitutes 85 to 95% by volume of the medium, and component B is 5 to 15% by volume.

The fluoride ion catalyst is provided by a fluoride compound which dissolves in component B to the extent of at least 0.001% by weight at 20° C. Suitable fluoride compounds are potassium, rubidium and cesium fluorides. A preferred fluoride compound is potassium fluoride, as its use results in higher yields of the desired product. The fluoride compound can be used in amounts of about 0.01 to 10 equivalents, preferably about 0.05 to 0.5 equivalents, per mole of IV or VIII employed as reactant.

The reaction of HFPO with reactants IV or VIII is exothermic. Reaction temperatures can range from about 0° to 100° C., with temperatures between 25° and 70° C. being preferred. Pressure is not critical, and subatmospheric and superatmospheric pressures are operable; pressures close to atmospheric are preferred. The pressure in the reaction vessel can be controlled by regulating the rate of supply of gaseous HFPO.

In the reaction dealt with herein, reactant IV first reacts with HFPO to form VIII, and VIII reacts with HFPO to form the desired product I. Product I, however, can further react with HFPO to form higher reaction products III where n is 3, 4, 5, etc. Loss of product I to the latter products III constitutes an irreversible loss of the very costly reactants IV and VIII and the costly HFPO to undesired products. Additionally, there is a competing reaction in this system wherein HFPO reacts with itself to form undesired HFPO oligomers, the production of which constitutes further loss of costly HFPO to undesired products.

Accordingly, reactant IV or VIII is preferably present in substantial excess at the beginning of the reaction.

In the reaction of IV to make I, two mole equivalents of HFPO are required. Inevitably, some VIII will be concurrently produced. The VIII so made can be recycled into the claimed process, either alone or in admixture with reactant IV, inasmuch as VIII and one mole equivalent of HFPO react to form I.

In the process of the invention, component A of the reaction medium is a relatively poor solvent for both the product I and for VIII. These substances employed as component A, when used alone as a reaction medium, result in a rate of reaction between HFPO and reactant IV or VIII such that there is considerable loss of HFPO to HFPO oligomers, and the rate of the desired reaction to I is so low as to make the process commercially unattractive.

By including the specified amount of component B along with component A, the rate of reaction of IV or VIII with HFPO is increased to the point where the process is commercially feasible. However, most substances employed as component B are such that relatively high amounts of product I or VIII dissolve in them. The amount of component B relative to component A is therefore chosen to provide an acceptable reaction rate without greatly increasing the solvent power of the combination of A and B for VIII or product I over the solvent power of A alone for VIII or product I. When the process is operated in this manner, as the reaction proceeds, a two-phase system results, with most of product I forming one component of the lower, heavier phase, along with minor amounts of other substances including by-products III where n is 3, 4, 5, etc. In this two-phase system, there is a reduced tendency for further reaction of I with HFPO to form the undesired products III where n is 3, 4, 5, etc. In this system, it is an easy matter to separate the two phases and isolate the product I from the lower phase; the upper, lighter phase can be recycled to the process, as is shown in the Examples.

The invention can be carried out as either a batch or continuous process. The invention lends itself particularly well to a continuous process in which the heavier phase is continuously removed and product I is recovered from it, and lower boiling materials recovered from the heavier phase are recycled to the process along with the total lighter phase.

The process of the invention provides a substance of known utility, and is a technically advanced process in that it provides the substance in substantially higher yield, and therefore at substantially lower cost, than does the prior known process.

To further illustrate the innovative aspects of the present invention, the following examples are provided. The results of the examples are assessed principally by the yield of Compound VII obtained, and to some extent by the yield of Compound VI (as it can be used to make Compound VII) and by the E/O ratio. The E/O ratio is the ratio of the number of moles of HFPO which become part of carboxylic ester products to the number of moles of HFPO which become part of HFPO oligomers, and is a measure of the relative rates of formation of the desired ester products and the undesired HFPO oligomers.

The reactions of all of the Examples were carried out under a nitrogen atmosphere. In each case a bath of warm water was used to initiate the reaction of hexafluoropropylene oxide with monomethyl difluoromalonyl fluoride and/or Compound VI, and then an ice bath was used to aid in controlling the internal temperature of the reacting system, in most cases to 30°–40° C.

EXAMPLE 1

A 250-ml round-bottom flask was fitted with a magnetic stirrer, gas inlet tube, thermometer, and Dry Ice cooled condenser. It was dried by flaming. The following were added to the flask in order: 45 ml adiponitrile, 5 ml tetraglyme, 73.5 g monomethyl difluoromalonyl fluoride (MMF), and 3.8 g potassium fluoride (KF). The mixture was stirred for 15 minutes, and then hexafluoropropylene oxide (HFPO) flow was started. The reaction was slow for about an hour, then became extremely rapid. The temperature rose to 35°–40° C. A total of 156 g HFPO was added. After a final stirring period, the mixture was filtered and separated into two liquid layers, 44.6 g upper layer and 226.7 g lower layer. The lower layer was analyzed by gas chromatography using a 5.5 m by 6.35 mm diameter column packed with a support of Gaschrome Z (manufactured by Applied Science Co.) carrying 20% by wt. of 3,3,3-trifluoropropylsilicone, starting at room temperature and heated at 10° C/minute. The results are given in Table II.

EXAMPLE 2

A 125-ml round-bottom flask was fitted with a magnetic stirrer, gas inlet tube, thermometer, and Dry Ice cooled condenser. The apparatus was dried by flaming, charged with 2 g KF, and again dried by flaming. Then 5 ml tetraglyme, 45 ml adiponitrile, and 32.2 g MMF were added. With stirring, 68 g HFPO was gradually introduced at 30°–40° C. The reaction was fast. The product was filtered, separated, and analyzed as in Example 1. The results are given in Table II.

EXAMPLE 3

To the apparatus of Example 2 was added 2 g KF. The apparatus was then dried by flaming, and there was added 5 ml tetraglyme, 45 ml adiponitrile, and 32.2 g MMF. With stirring, 68 g HFPO was added gradually. The reaction was very slow at first, but the final rate was fast. The reaction mixture was filtered to facilitate separation, separated into two layers, and analyzed as in Example 1. The results are given in Table II.

EXAMPLE 4

The apparatus of Example 2 was charged with 2.0 g KF and dried by flaming. Then 5 ml tetraglyme, 45 ml adiponitrile, and 32.2 g MMF were added. Stirring was started and 75 g HFPO was added at a rate to keep the temperature at 30°–40° C. Reaction was rapid. The results are shown in Table II.

EXAMPLE 5

To the apparatus of Example 2 was added 2.0 g KF, and the apparatus was flamed to dry it. Then 10 ml tetraglyme, 40 ml adiponitrile, and 32.2 g MMF were added, the latter after stirring started. Then 68 g HFPO was added gradually at 30°–40° C. Reaction was very rapid. After the reaction period the product was filtered and separated to give 49.1 g upper layer and 91.3 g lower layer, which was analyzed as in Example 1. The results are given in Table II.

EXAMPLE 6

The same apparatus as in Example 1 was charged with 5.3 g CsF and dried by flaming. Then 5 ml tetraglyme, 45 ml adiponitrile and 32.2 g MMF were added. The mixture was stirred at 40° C. and almost all the CsF dissolved. The mixture was cooled to 2° C. and HFPO (68 g) was added gradually, keeping the temperature below 5° with an ice bath. Reaction was rapid. The product was filtered and separated into two layers. The lower layer was analyzed as in Example 1. The results are given in Table II.

EXAMPLE 7

The apparatus was the same as in Example 2. After 2.0 g KF was added, the apparatus was again flamed to dryness. Then 10 ml butyrolactone, 40 ml adiponitrile and 32.2 g MMF were added. The mixture was stirred as 51 g HFPO was added. The reaction started slowly but then ran rapidly. The product was filtered and separated into layers, and the lower layer was analyzed as in Example 1. The results are given in Table II.

EXAMPLE 8

This example is intended to simulate a continuous process for preparing Compound VII.

A 300-ml round-bottomed flask was fitted with a magnetic stirrer, gas inlet tube, thermometer, and Dry Ice cooled condenser. After addition of 2 g KF, the apparatus was dried by flaming. Then 10 ml butyrolactone, 40 ml adiponitrile, and 32.2 g distilled MMF were added. The mixture was stirred while 68 g HFPO was added at 30°–40° C. Reaction rate was good. The mixture was stirred another 2 hours, then stirring was stopped and the lower layer sampled. The yield of VII based on HFPO was 44.2%. The yield of VII from MMF was 43.8%.

Another 32.2 g distilled MMF was added, and HFPO was added with stirring. Reaction was slow at first at 30°–40° C., then rapid. The HFPO added was 68 g. Stirring was stopped and the lower layer was sampled and analyzed. Yield of VII based on HFPO was 37.1% and based on MMF was 36.8%.

Then another 32.2 g distilled MMF was added and 68 g more HFPO was added gradually with stirring at 30°–40°. Reaction was fast. After further stirring, the mixture was filtered, separated into layers, and analyzed as in Example 1. The results are given in Table II.

EXAMPLE 9

A 200-ml round-bottomed flask was fitted with a magnetic stirrer, gas inlet tube, thermometer and Dry Ice cooled condenser. After addition of 2 g KF, the apparatus was dried by flaming. Then 5 ml tetraglyme, 45 ml tetramethylenesulfone and 32.2 g MMF were added. The mixture was stirred while 68 g HFPO was added at 30°–40° C. Reaction was slow. The mixture was filtered, separated into layers and analyzed as in Example 1. The results are given in Table II.

TABLE II

| Example | Yield (%) Based on HFPO to VI | Yield (%) Based on HFPO to VII | Yield (%) Based on V to VI | Yield (%) Based on V to VII | E/O Ratio |
|---|---|---|---|---|---|
| 1 | 23.5 | 43.8 | 46.1 | 43.1 | 6.02 |
| 2 | 16.9 | 42.5 | 33.9 | 42.6 | 9.62 |
| 3 | 21.4 | 39.2 | 43.1 | 39.5 | 5.75 |
| 4 | 9.1 | 42.5 | 20.0 | 46.5 | 6.67 |
| 5 | 15.3 | 40.5 | 30.6 | 40.6 | 8.00 |
| 6 | 21.0 | 33.7 | 41.7 | 33.4 | 3.65 |
| 7 | 31.3 | 34.8 | 50.5 | 28.1 | 5.08 |
| 8 | 21.4 | 35.2 | 42.4 | 34.9 | 3.50 |
| 9 | 18.7 | 32.3 | 39.2 | 33.9 | 3.65 |

EXAMPLE 10

The apparatus of Example 2 was charged with 2.0 KF and dried by flaming. Then 5 ml tetraglyme, 45 ml adiponitrile, and 64.4 g of methyl perfluoro(4-oxa-5-fluoroformylhexanoate) (Compound VI) were added. With stirring, 40 g HFPO was added gradually at 30°–40° C. Reaction was rapid. The yield of VII based on HFPO was 39.3% and based on VI was 62.1%, and the E/O ratio was 2.78.

EXAMPLE 11

To the apparatus of Example 2 was added 2.0 g KF catalyst and the apparatus was flamed to dry it. Then 25 ml butyrolactone, 25 ml of adiponitrile, and 64.4 g of Compound VI were added. The temperature was kept at 10° C. while 27 g of HFPO was added. The reaction proceeded well, giving a wine-colored product. After filtration to facilitate phase separation, the layers were separated and the lower layer analyzed as in Example 1. The yield of Compound VII was 70.7% based on Compound VI, and 56.5% based on HFPO. The E/O ratio was 7.04.

EXAMPLE 12

To the apparatus described in Example 1 was charged 5.3 g CsF, and the apparatus was dried by flaming. Then 49 ml adiponitrile, 1 ml tetraglyme, 64.4 ml Compound VI, and 32.2 g MMF were charged. Stirring caused solution of most of the CsF. Two liquid phases were present. HFPO was added gradually at 20° C. until 68 g had been added. Reaction was fast. At the end of the reaction, the product was filtered and separated into two layers. The lower layer was analyzed as in Example 1. The results were as follows:

Yield of VII based on MMF; 33.7%;
Yield of VII based on HFPO; 33.9%;
Yield of VI based on MMF; 33.9%;
Yield of VI based on HFPO; 17.1%;
E/O ratio; 1.63.

That the small amount of tetraglyme had a beneficial effect is shown by comparison with the following Example A.

COMPARATIVE EXAMPLE A

Example 12 was substantially repeated, except that 50 ml adiponitrile was used, and no tetraglyme was included. The results were as follows:

Yield of VII based on MMF; 32.8%;
Yield of VII based on HFPO; 33.1%;
Yield of VI based on MMF; 29.1%;
Yield of VI based on HFPO; 14.6%;
E/O ratio; 1.62.

EXAMPLE 13

This example demonstrates that part of the crude reaction product can be recycled.

The apparatus of Example 5 was charged with 2 g KF and dried by flaming. The entire upper layer from Example 5 was charged, along with another 32.2 g MMF. HFPO (68 g) was gradually added at 30°–40°. Reaction was very fast. The product was filtered. separated, and analyzed as in Example 1.

The results were as follows:
Yield of VII based on MMF; 41.0%;
Yield of VII based on HFPO; 40.6%;
Yield of VI based on MMF; 34.7%
Yield of VI based on HFPO; 17.2%;
E/O ratio; 9.26.

INDUSTRIAL APPLICABILITY

The invention provides an improved process for the preparation of alkyl perfluoro(4,7-dioxa-5-methyl-8-fluoroformylnonanoates), which are intermediates to alkyl perfluoro(4,7-dioxa-5-methylnon-8-eneoates) (compounds II). The latter form valuable copolymers with fluorinated olefins such as tetrafluoroethylene, the copolymers being useful as ion exchange material, e.g., in the form of membranes for separating the anode and cathode compartment of a chloralkali cell.

I claim:
1. In a process for preparing a product compound of the formula

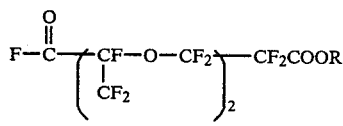

where R is alkyl of 1-6 carbon atoms, wherein a reactant of the formula

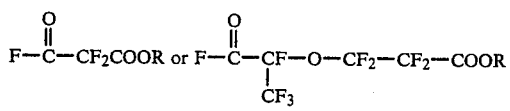

where R is as defined above is contacted with hexafluoropropylene oxide in the presence of a fluoride compound which provides fluoride ion catalyst, the improvement comprising contacting said reactant with hexafluoropropylene oxide and said catalyst in the presence of a medium consisting essentially of two components, component A being 50 to 98% by volume of an aprotic liquid dinitrile in which methyl perfluoro (4-oxa-5-fluoroformylhexanoate) dissolves to the extent of less than 10 g/100 g of A at 20° C. or tetramethylenesulfone, and component B being 50 to 2% by volume of an aprotic liquid glyme, lactone or mononitrile in which said fluoride compound is soluble to the extent of at least 0.001% by weight at 20° C. and in which methyl perfluoro(4-oxa-5-fluoroformylhexanoate) dissolves to the extent of at least 10 g/100 g of B at 20° C., separating a heavier phase which contains said product compound from a lighter phase, and separating said product compound from said heavier phase.

2. The process of claim 1 wherein component A is such that methyl perfluoro(4-oxa-5-fluoroformylhexanoate) dissolves in it to the extent of no more than 6 g/100 g of A at 20° C., and component B is such that methyl perfluoro(4-oxa-5-fluoroformylhexanoate) dissolves in it to the extent of at least 20 g/100 g of B at 20° C.

3. The process of claim 2 wherein said medium consists of 85 to 98% by volume of component A and 15 to 2% by volume of component B.

4. The process of claim 3 wherein component B is such that methyl perfluoro(4-oxa-5-fluoroformylhexanoate) dissolves in it to the extent of at least 100 g/100 g of B at 20° C.

5. The process of claim 4 wherein said medium consists of 85 to 95% by volume of component A and 15 to 5% by volume of component B.

6. The process of claim 5 wherein component A is a dinitrile or tetramethylene sulfone, and component B is a glyme.

7. The process of claim 6 wherein component A is adiponitrile, and component B is bis[2-(2-methoxyethoxy)ethyl] ether.

8. The process of claim 1 wherein said fluoride compound is selected from the group consisting of potassium, rubidium and cesium fluorides, said component A is selected from the group consisting of malononitrile, succinonitrile, glutaronitrile, adiponitrile, methylmalononitrile, pimelonitrile, suberonitrile, phthalonitrile and tetramethylenesulfone, and said component B is selected from the group consisting of monoethyleneglycol dimethyl ether, diethyleneglycol dimethyl ether, triethyleneglycol dimethyl ether, tetraethyleneglycol dimethyl ether, 4-butyrolactone, 5-valerolactone, 6-caprolactone, acetonitrile and propionitrile.

9. The process of claim 7 wherein said fluoride compound is potassium fluoride.

10. The process of claim 1, 4, 7 or 9 wherein R is -CH$_3$.

* * * * *

UNITED STATES PATENT OFFICE
CERTIFICATE OF CORRECTION

PATENT NO. : 4,345,092

DATED : August 17, 1982

INVENTOR(S) : Paul R. Resnick

It is certified that error appears in the above-identified patent and that said Letters Patent are hereby corrected as shown below:

On the cover sheet, left column, item [54], and in column 1, lines 2-4, the title, "PROCESS FOR ALKYL PERFLUORO(4,7-DIOXA-5-METHYL-8-FLUOROFORMYLNONANOATE" should read -- PROCESS FOR ALKYL PERFLUORO(4,7-DIOXA-5-METHYL-8-FLUOROFORMYLNONANOATE) --.

Column 9, lines 1-6, that portion of the formula reading $-\underset{\underset{CF_2}{|}}{CF}-$ should read $-\underset{\underset{CF_3}{|}}{CF}-$ .

Signed and Sealed this

Twelfth Day of June 1984

[SEAL]

*Attest:*

*Attesting Officer*

GERALD J. MOSSINGHOFF

*Commissioner of Patents and Trademarks*